United States Patent
Chasin et al.

[19]

[11] Patent Number: 6,075,016
[45] Date of Patent: Jun. 13, 2000

[54] 6,5-FUSED AROMATIC RING SYSTEMS HAVING ENHANCED PHOSPHODIESTERASE IV INHIBITORY ACTIVITY

[75] Inventors: Mark Chasin, Manalapan, N.J.; David Cavalla, Cambridge, United Kingdom; Peter Hofer, Liestal, Switzerland; Andre Gehrig; Peter Wintergerst, both of Basel, Switzerland

[73] Assignee: Euro-Celtique S.A., Luxembourg, Luxembourg

[21] Appl. No.: 08/833,893

[22] Filed: Apr. 10, 1997

Related U.S. Application Data

[60] Provisional application No. 60/014,917, Apr. 10, 1996.

[51] Int. Cl.$^7$ .................. A61K 31/40; A61K 31/435; C07D 471/04; C07D 498/04
[52] U.S. Cl. .................. 514/183; 514/243; 514/247; 514/248; 514/249; 514/300; 514/302; 514/303; 544/184; 544/236; 544/264; 544/278; 544/280; 544/179; 546/113; 546/115; 546/118
[58] Field of Search .................. 514/338, 375, 514/183, 243, 247, 248, 249, 300, 302, 303; 546/271.7, 113, 115, 118; 548/217; 544/179, 184, 236, 264, 278, 280

[56] References Cited

U.S. PATENT DOCUMENTS

| | | | |
|---|---|---|---|
| Re. 31,429 | 10/1983 | Tull et al. | 544/277 |
| 2,320,654 | 6/1943 | Riester | 95/7 |
| 2,691,654 | 10/1954 | Hitchings | 260/247.5 |
| 2,844,577 | 7/1958 | Acker | 260/254 |
| 2,903,455 | 9/1959 | Strong et al. | 260/252 |
| 2,956,998 | 10/1960 | Baizer | 260/252 |
| 2,957,875 | 10/1960 | Lyttle et al. | 260/252 |
| 2,966,488 | 12/1960 | Shive et al. | 260/252 |
| 3,079,378 | 2/1963 | Schroeder | 260/211.5 |
| 3,129,225 | 4/1964 | Shapiro | 260/247.2 |
| 3,135,753 | 6/1964 | Hitchings | 540/265 |
| 3,136,771 | 6/1964 | Liechti et al. | 260/296 |
| 3,215,696 | 11/1965 | Denayer | 260/252 |
| 3,225,046 | 12/1965 | Zwahlen | 260/252 |
| 3,262,929 | 7/1966 | Okubu et al. | 260/240 |
| 3,470,164 | 9/1969 | Takamatsu | 260/240 |
| 3,491,091 | 1/1970 | Berger | 260/240 |
| 3,491,106 | 1/1970 | Freyermuth | 260/304 |
| 3,494,919 | 2/1970 | Collins et al. | 260/240 |
| 3,516,997 | 6/1970 | Takano et al. | 260/243 |
| 3,541,100 | 11/1970 | Ramirez et al. | 260/286 |
| 3,551,554 | 12/1970 | Herschler | 424/7 |
| 3,574,218 | 4/1971 | Hideg et al. | 260/293.4 |
| 3,586,670 | 6/1971 | Brenneisen | 260/240 |
| 3,590,029 | 6/1971 | Koch | 260/211.5 |
| 3,626,018 | 12/1971 | Taylor | 260/670 |
| 3,636,039 | 1/1972 | Gruenman et al. | 260/309.7 |
| 3,647,812 | 3/1972 | Smith | 260/304 |
| 3,658,799 | 4/1972 | Eardley | 260/243 C |
| 3,666,769 | 5/1972 | Jones | 260/304 |
| 3,669,979 | 6/1972 | Freyermuth | 260/304 |
| 3,674,781 | 7/1972 | Schinzel et al. | 260/240 |

(List continued on next page.)

FOREIGN PATENT DOCUMENTS

| | | |
|---|---|---|
| 994351 | 8/1976 | Canada . |
| 0018136 | 10/1980 | European Pat. Off. . |
| 0178413 | 4/1986 | European Pat. Off. . |
| 0191313 | 8/1986 | European Pat. Off. . |
| 0203721 | 12/1986 | European Pat. Off. . |
| 0256692 | 2/1988 | European Pat. Off. . |
| 0258191 | 3/1988 | European Pat. Off. . |
| 0343643 | 11/1989 | European Pat. Off. . |
| 360701 | 3/1990 | European Pat. Off. . |
| 0369744 | 5/1990 | European Pat. Off. . |
| 0386683 | 9/1990 | European Pat. Off. . |
| 0389282 | 9/1990 | European Pat. Off. . |
| 0400799 | 12/1990 | European Pat. Off. . |

(List continued on next page.)

OTHER PUBLICATIONS

CA Select: "Anti–Inflammatory Agents & Arthritis" Issue 7, 1996, p. 26.
CA of "1–Pharmacology", vol. 106, 1987, p. 61.
CA Selects: "Allergy & Antiallergic Agents", Issue 5, 1996, pp. 17 and 19.
CA Selects: "Allergy & Antiallergic Agents", Issue 21, 1995, p. 13.
CA Selects: Anti–Inflammatory Agents & Arthritis, Issue 23, 1995, p. 17 and 23.
CA Selects: "Anti–Inflammatory Agents & Arthritis", Issue 25, 1996, (1 page).
CA 171494, 171495 and KG–2683 of Annual Drug Data Report 1991 (1 sheet).
Ronald E. Weishaar, et al., Subclasses of Cyclic GMP–Specific phosphodiesterase and their role in regulating the effects of atrial natriuretic factor, Dept. Of Pharmacology, Parke–Davis Pharmaceutical Research Division, Warner–Lambert Co. Hypertension, vol. 15, No. 5, May 1990.
"Differential modulation of tissue function and therapeutic potential selective inhibitors of cyclic nucleotide phosphodiesterase isoenzymes", C. David Nicholson, R.A. John Challiss and Mohammed Shahid, 1991, Elsevier Science Publishers Ltd. (UK), TIPS 12:19–27.

(List continued on next page.)

*Primary Examiner*—Joseph McKane
*Attorney, Agent, or Firm*—Davidson, Davidson & Kappel, LLC

[57] ABSTRACT

Novel compounds which are effective PDE IV inhibitors are disclosed. The compounds possess improved PDE IV inhibition as compared to theophylline or rolipram, with improved selectivity with regard to, e.g., PDE V inhibition. The present invention includes compounds of Formula I:

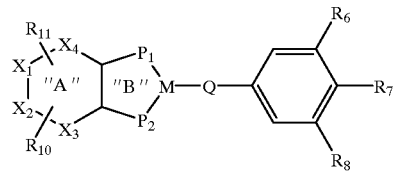

Formula I

8 Claims, No Drawings

U.S. PATENT DOCUMENTS

| | | | |
|---|---|---|---|
| 3,681,328 | 8/1972 | Kurita | 260/243 C |
| 3,686,238 | 8/1972 | Zaffaroni | 260/399 |
| 3,706,834 | 12/1972 | Scheilenbaum et al. | 424/272 |
| 3,923,833 | 12/1975 | Gruenman et al. | 260/340.5 |
| 3,962,452 | 6/1976 | Evans et al. | 424/272 |
| 4,020,165 | 4/1977 | Hubbard | 514/367 |
| 4,025,636 | 5/1977 | Dunwell et al. | 424/269 |
| 4,025,637 | 5/1977 | Dunwell | 424/272 |
| 4,107,306 | 8/1978 | Voorhees | 424/248.51 |
| 4,146,721 | 3/1979 | Rainer | 548/374 |
| 4,167,628 | 9/1979 | Kormany | 542/454 |
| 4,233,303 | 11/1980 | Bergstrand et al. | 424/253 |
| 4,241,063 | 12/1980 | Naito et al. | 424/253 |
| 4,241,168 | 12/1980 | Arai | 430/503 |
| 4,308,278 | 12/1981 | Schneider et al. | 424/273 R |
| 4,361,699 | 11/1982 | Rasmusson et al. | 544/277 |
| 4,407,802 | 10/1983 | Graham et al. | 424/253 |
| 4,416,892 | 11/1983 | Dawson | 424/272 |
| 4,454,138 | 6/1984 | Goring | 424/253 |
| 4,469,698 | 9/1984 | Philippossian et al. | 424/253 |
| 4,495,195 | 1/1985 | Beck et al. | 514/406 |
| 4,616,020 | 10/1986 | Furrer et al. | 514/264 |
| 4,652,654 | 3/1987 | Verga et al. | 548/217 |
| 4,684,656 | 8/1987 | Atwal | 514/274 |
| 4,684,728 | 8/1987 | Möhring | 544/182 |
| 4,710,503 | 12/1987 | Hofer | 514/263 |
| 4,732,978 | 3/1988 | Kreft et al. | 546/152 |
| 4,755,517 | 7/1988 | Bruns et al. | 514/263 |
| 4,757,124 | 7/1988 | Koyanagi | 526/62 |
| 4,769,377 | 9/1988 | Snyder et al. | 514/263 |
| 4,770,990 | 9/1988 | Nakamura | 430/564 |
| 4,775,695 | 10/1988 | Cragoe, Jr. et al. | 514/637 |
| 4,803,216 | 2/1989 | Appleton et al. | 514/407 |
| 4,810,719 | 3/1989 | Appleton et al. | 514/406 |
| 4,826,868 | 5/1989 | Wachter et al. | 514/407 |
| 4,831,152 | 5/1989 | Itoh et al. | 548/224 |
| 4,851,321 | 7/1989 | Takagi | 430/264 |
| 4,868,183 | 9/1989 | Kanai et al. | 514/255 |
| 4,874,869 | 10/1989 | Ueda et al. | 548/309 |
| 4,883,801 | 11/1989 | Nathanson | 514/263 |
| 4,910,211 | 3/1990 | Imamura et al. | 514/367 |
| 4,918,074 | 4/1990 | Tsuda et al. | 514/258 |
| 4,925,847 | 5/1990 | Hofer | 514/263 |
| 4,965,169 | 10/1990 | Hirano | 430/264 |
| 4,971,972 | 11/1990 | Doll et al. | 514/265 |
| 4,981,857 | 1/1991 | Daluge | 574/263 |
| 4,994,363 | 2/1991 | Koya et al. | 430/564 |
| 5,010,081 | 4/1991 | Hofer | 514/263 |
| 5,047,411 | 9/1991 | Takasugi et al. | 514/300 |
| 5,057,517 | 10/1991 | Johnston et al. | 514/254 |
| 5,068,236 | 11/1991 | Suzuki et al. | 514/263 |
| 5,091,431 | 2/1992 | Tulshian et al. | 514/262 |
| 5,098,464 | 3/1992 | Barton et al. | 71/92 |
| 5,110,818 | 5/1992 | Allgeier | 514/261 |
| 5,114,835 | 5/1992 | Sakaoue | 430/393 |
| 5,116,717 | 5/1992 | Matsushita | 430/264 |
| 5,117,830 | 6/1992 | McAfee et al. | 128/654 |
| 5,139,921 | 8/1992 | Takagi et al. | 430/264 |
| 5,177,074 | 1/1993 | Allen et al. | 514/234 |
| 5,177,085 | 1/1993 | Naef | 424/253 |
| 5,190,942 | 3/1993 | Poss | 514/235.8 |
| 5,191,084 | 3/1993 | Bagli et al. | 546/279 |
| 5,206,255 | 4/1993 | Ubasawa et al. | 514/374 |
| 5,264,589 | 11/1993 | Corey | 548/51 |
| 5,270,206 | 12/1993 | Saccomano | 435/280 |
| 5,288,896 | 2/1994 | Capiris et al. | 560/27 |
| 5,290,782 | 3/1994 | Suzuki et al. | 514/263 |
| 5,322,847 | 6/1994 | Marfat et al. | 514/303 |
| 5,342,835 | 8/1994 | Pepin et al. | 514/227.5 |
| 5,369,085 | 11/1994 | Hosokawa et al. | 504/249 |
| 5,424,432 | 6/1995 | Fredenburgh et al. | 546/118 |
| 5,434,150 | 7/1995 | Austel et al. | 514/228.5 |
| 5,436,258 | 7/1995 | Blake et al. | 514/372 |
| 5,449,686 | 9/1995 | Christensen, IV | 514/330 |
| 5,451,596 | 9/1995 | Ullrich | 514/375 |
| 5,496,853 | 3/1996 | Shiota et al. | 514/469 |
| 5,602,157 | 2/1997 | Christensen, IV | 514/362 |
| 5,602,173 | 2/1997 | Christensen, IV | 514/475 |
| 5,631,260 | 5/1997 | Belardinelli et al. | 514/263 |
| 5,637,708 | 6/1997 | Hogle et al. | 546/140 |
| 5,641,789 | 6/1997 | Marfat | 514/314 |
| 5,665,737 | 9/1997 | Cavalla et al. | 514/338 |

FOREIGN PATENT DOCUMENTS

| | | |
|---|---|---|
| 0417790 | 3/1991 | European Pat. Off. . |
| 0435811 | 7/1991 | European Pat. Off. . |
| 0463756 | 1/1992 | European Pat. Off. . |
| 0470805 | 2/1992 | European Pat. Off. . |
| 0497564 | 8/1992 | European Pat. Off. . |
| 0511865 | 11/1992 | European Pat. Off. . |
| 0536713 | 4/1993 | European Pat. Off. . |
| 0590919 | 4/1994 | European Pat. Off. . |
| 0619316 | 10/1994 | European Pat. Off. . |
| 0623607 | 11/1994 | European Pat. Off. . |
| 0645389 | 3/1995 | European Pat. Off. . |
| 0671389 | 9/1995 | European Pat. Off. . |
| 0675124 | 10/1995 | European Pat. Off. . |
| 0685474 | 12/1995 | European Pat. Off. . |
| 0685479 | 12/1995 | European Pat. Off. . |
| 0728759 | 8/1996 | European Pat. Off. . |
| 0731099 | 9/1996 | European Pat. Off. . |
| 0779291 | 6/1997 | European Pat. Off. . |
| 835818 | 2/1961 | France . |
| 1548252 | 12/1968 | France . |
| 2104932 | 6/1972 | France . |
| 2008464 | 9/1970 | Germany . |
| 2314676 | 10/1973 | Germany . |
| 2346034 | 4/1974 | Germany . |
| 51-54587 | 5/1976 | Japan . |
| 57-21375 | 2/1982 | Japan . |
| 559056 | 3/1993 | Japan . |
| 6211856 | 8/1994 | Japan . |
| 7118247 | 5/1995 | Japan . |
| 717952 | 7/1995 | Japan . |
| 8113567 | 5/1996 | Japan . |
| 215948 | 10/1989 | New Zealand . |
| 1077689 | 8/1967 | United Kingdom . |
| 1260793 | 1/1972 | United Kingdom . |
| 1498705 | 1/1978 | United Kingdom . |
| 1561005 | 2/1980 | United Kingdom . |
| 2041359 | 9/1980 | United Kingdom . |
| 1580782 | 12/1980 | United Kingdom . |
| 2283488 | 5/1995 | United Kingdom . |
| 8601724 | 3/1986 | WIPO . |
| 9631487 | 10/1986 | WIPO . |
| 9100858 | 1/1991 | WIPO . |
| 9200968 | 1/1992 | WIPO . |
| 9205175 | 4/1992 | WIPO . |
| 9205176 | 4/1992 | WIPO . |
| 9207567 | 5/1992 | WIPO . |
| 9219594 | 11/1992 | WIPO . |
| 9307111 | 4/1993 | WIPO . |
| 9307141 | 4/1993 | WIPO . |
| 9314081 | 7/1993 | WIPO . |
| 9314082 | 7/1993 | WIPO . |
| 9315044 | 8/1993 | WIPO . |
| 9315045 | 8/1993 | WIPO . |
| 9318024 | 9/1993 | WIPO . |
| 9319747 | 10/1993 | WIPO . |
| 9319749 | 10/1993 | WIPO . |
| 9319750 | 10/1993 | WIPO . |
| 9319751 | 10/1993 | WIPO . |

| | | | |
|---|---|---|---|
| 9322287 | 11/1993 | WIPO . | |
| 9325517 | 12/1993 | WIPO . | |
| 9402465 | 2/1994 | WIPO . | |
| 9410118 | 5/1994 | WIPO . | |
| 9412461 | 6/1994 | WIPO . | |
| 9414742 | 7/1994 | WIPO . | |
| 9414800 | 7/1994 | WIPO . | |
| 9420446 | 9/1994 | WIPO . | |
| 9420455 | 9/1994 | WIPO . | |
| 9420460 | 9/1994 | WIPO . | |
| 9422859 | 10/1994 | WIPO . | |
| 9425437 | 11/1994 | WIPO . | |
| 9500139 | 1/1995 | WIPO | A61K 31/275 |
| 9501338 | 1/1995 | WIPO . | |
| 9503297 | 2/1995 | WIPO . | |
| 9503794 | 2/1995 | WIPO . | |
| 9504045 | 2/1995 | WIPO . | |
| 9504046 | 2/1995 | WIPO . | |
| 9508534 | 3/1995 | WIPO . | |
| 9509623 | 4/1995 | WIPO . | |
| 9509624 | 4/1995 | WIPO . | |
| 9509627 | 4/1995 | WIPO . | |
| 9509836 | 4/1995 | WIPO . | |
| 9509837 | 4/1995 | WIPO . | |
| 9604253 | 5/1995 | WIPO . | |
| 9514667 | 6/1995 | WIPO . | |
| 9517386 | 6/1995 | WIPO . | |
| 9517392 | 6/1995 | WIPO . | |
| 9517399 | 6/1995 | WIPO . | |
| 9522520 | 8/1995 | WIPO . | |
| 9523148 | 8/1995 | WIPO . | |
| 9527692 | 10/1995 | WIPO . | |
| 9535281 | 12/1995 | WIPO . | |
| 9535282 | 12/1995 | WIPO . | |
| 9535283 | 12/1995 | WIPO . | |
| 9535284 | 12/1995 | WIPO . | |
| 9535285 | 12/1995 | WIPO . | |
| 9600215 | 1/1996 | WIPO . | |
| 9603396 | 2/1996 | WIPO . | |
| 9603399 | 2/1996 | WIPO . | |
| 9612720 | 5/1996 | WIPO . | |
| 9620157 | 7/1996 | WIPO . | |
| 9620158 | 7/1996 | WIPO . | |
| 9620174 | 7/1996 | WIPO . | |
| 9620175 | 7/1996 | WIPO . | |
| 9624350 | 8/1996 | WIPO . | |
| 9631476 | 10/1996 | WIPO . | |
| 9631485 | 10/1996 | WIPO . | |
| 9631486 | 10/1996 | WIPO . | |
| 9628430 | 11/1996 | WIPO . | |
| 9636595 | 11/1996 | WIPO . | |
| 9636596 | 11/1996 | WIPO . | |
| 9636611 | 11/1996 | WIPO . | |
| 9636624 | 11/1996 | WIPO . | |
| 9636625 | 11/1996 | WIPO . | |
| 9636626 | 11/1996 | WIPO . | |
| 9636638 | 11/1996 | WIPO . | |
| 9638150 | 12/1996 | WIPO . | |
| 9703070 | 1/1997 | WIPO . | |
| 9703967 | 2/1997 | WIPO . | |
| 9712887 | 4/1997 | WIPO . | |
| 9712888 | 4/1997 | WIPO . | |
| 9720833 | 6/1997 | WIPO . | |
| 9722585 | 6/1997 | WIPO . | |
| 9722586 | 6/1997 | WIPO . | |
| 9723457 | 7/1997 | WIPO . | |
| 9723460 | 7/1997 | WIPO . | |
| 9723461 | 7/1997 | WIPO . | |
| 9724334 | 7/1997 | WIPO . | |
| 9725312 | 7/1997 | WIPO . | |
| 9728143 | 8/1997 | WIPO . | |
| 9728144 | 8/1997 | WIPO . | |
| 9728145 | 8/1997 | WIPO . | |
| 9728146 | 8/1997 | WIPO . | |
| 9728147 | 8/1997 | WIPO . | |
| 9728148 | 8/1997 | WIPO . | |
| 9728155 | 8/1997 | WIPO . | |

OTHER PUBLICATIONS

"Phosphodiesterase inhibitors: new opportunities for the treatment of asthma", Theodore J. Torphy, Bradley J. Undem, *Thorax* 1991; 46:512–523.

"Novel phosphodiesterase inhibitors for the therapy of asthma", Theodore J. Torphy, George P. Livi and Siegfried B. Christensen, DN&P 6(4), May 1993 pp. 203–214.

"Assay of cyclic nucleotide phosphodiesterase and resolution of multiple molecular forms of the enzyme", W. Joseph Thompson, Wesley L. Terasaki, Paul M. Epstein, Samuel J. Strada, Advances in Cyclic Nucleotide Research, vol. 10, 1979, pp. 69–92.

"Identification, characterization and functional role of phosphodiesterase isozymes in human airway smooth muscle", Theodore J. Torphy, Bradley J. Undem, Lenora B. Cieslinski, Mark A. Luttmann, Martin L. Reeves and Douglas W.P. Hay, The Journal of Pharmacology and Experimental Therapeutics, 1993, vol. 265, No. 3, 1213–1223.

"The PDE IV family of calcium–independent phosphodiesterase enzymes", John A. Lowe III and John B. Cheng, Drugs of the Future, 1992, 17(9): 799–807.

"Could isoenzyme–selective phosphodiesterase inhibitors render bronchodilator therapy redundant in the treatment of bronchial asthma?", Mark A. Giembycz, Biochemical Pharmacology, 1992, vol. 43, No. 10 pp. 2041–2051.

"Differential pharmacologic sensitivity of cyclic nucleotide phosphodiesterase isozymes from cardiac muscle, arterial and airway smooth muscle", Paul J. Silver, Linda T. Hamel, Mark H. Perrone, Ros G. Bently, Cynthia R. Bushover and Dale B. Evans, European Journal of Pharmacology, 150 (1988) 85–94, Elsevier.

"Structure–Activity Relationships in a Series of 6–Thioxanthines with Bronchodilator and Coronary Dilator Properties", A.K. Armitrage, Janet Boswood and B.J. Large, Brit. J. Pharma. 1961, 17:196–207.

"The Synthesis of Some 6 Thioxanthines", K.R.H. Wooldrige and R. Slack, J. Chem. Soc. 1962, Annex IV:1863–1868.

Chemical Abstracts, vol. 85, No. 1 (Jul. 9, 1976) 5692s (Enoki).

Chemical Abstracts, vol. 84, No. 25 (Jun. 21, 1976) 180299v (Enoki).

Chemical Abstracts, vol. 86, No. 7 (Feb. 14, 1977) 43746r (Aida).

Isomura et al., "Studies on the synthesis and anti–inflammatory activity of 2,6–Di–tert–butylphenols with a heterocyclic group at the 4–position.I", vol. 31, No. 9, pp. 3168–3178 (1983).

Chemical Abstracts 103:37354, 1985 (Nagarajan).

Chemical Abstracts 116:255335, 1992 (Bender).

Itaya, *Tetrahedron Letters*, vol. 23, No. 21 (1982), pp. 2203–2204.

Reitz, *Journal of Organic Chemistry*, vol. 55, No. 22 (Oct. 26, 1990), pp. 5761–5766.

Chemical Abstracts 88: 51054, 1977 (Ninomiya).

Chemical Abstracts, vol. 82 (19) May 12, 1975, Abstract #125358x (Kazimierezuk).

Chemical Abstracts 114: 246982, 1990 (Naruto).

"Controlled Interaction between Nucleic Acid Bases. Intramolecular Stacking Interactions between Two Adenine Rings", Nelson J. Leonard, et al.; Journal of the American Chemical Society, 95:12, Jun. 13, 1973, pp. 4010–4016.

Chemical Abstracts 92: 6207, 1977 (Pirisino).

Ronald E. Weishaar, et al., Multiple molecular forms of cyclic nucleotide phosphodiesterase in cardiac and smooth muscle and in platelets, Biochemical Pharmacology, vol. 35, No. 5., pp. 787–800, 1986.

Chemical Abstracts 116:173873 (1979) Girshovich.

J. A. Montgomery, et al., "Synthesis of Potential Anticancer Agents. XIX. 2–Substituted $N^6$–Alkyladenines" (1959) J.A.C.S. vol. 81, pp. 3963–3967.

Chemical Abstracts 53:6243 (1957) Elion.

T. Fuji, et al. "3–Substituted Adenines. In Vitro Enzyme Inhibition and Antiviral Activity", (1979) Journal of Medicinal Chemistry, vol. 22, No. 2, pp. 126–129.

Burger, Ed. "Medicinal Chemistry" 2d ed. pp. 42–43, Interscience, New York, New York (1960).

Ram et al., Indian J. Chem., Sect. B (1993), 32B(9), 924–8.

Salem et al., CA 117:26410 (1992).

Ram et al., CA 116:6463 (1992).

Nikolyukin et al., CA 114:122145 (1991).

Pepin et al., CA 114:96801 (1991).

Murray et al., CA 112:198208 (1990).

Agrawal, CA 109:54701 (1988).

Tominaga et al., CA 107:236648 (1987).

Vishwakarma et al., CA 104:168404 (1986).

Reddy et al., CA 104:168228 (1986).

Feeny, CA 92:17174 (1980).

De Lucia et al., CA 68:96797 (1968).

Derwent Abstract of JP 1200246, published Aug. 11, 1989.

Derwent Abstract of JP 1245256, published Sep. 29, 1989.

Derwent Abstract of JP 1231049, published Sep. 14, 1989.

Derwent Abstract of JP 1229251, published Sep. 12, 1989.

Derwent Abstract of JP 1225951, published Sep. 8, 1989.

Derwent Abstract of JP 1224756, published Sep. 7, 1989.

Derwent Abstract of JP 1224755, published Sep. 7, 1989.

Derwent Abstract of JP 1219748, published Sep. 1, 1989.

Derwent Abstract of JP 1216353, published Aug. 20, 1989.

Derwent Abstract of JP 1214845, published Aug. 29, 1989.

Derwent Abstract of JP 1093733, published Apr. 12, 1989.

Derwent Abstract of JP 63271246, published Nov. 9, 1988.

Derwent Abstract of JP 58111034, published Jul. 1, 1983.

6,5-FUSED AROMATIC RING SYSTEMS HAVING ENHANCED PHOSPHODIESTERASE IV INHIBITORY ACTIVITY

This application is based on provisional application Ser. No. 60/014,917 filed Apr. 10, 1996.

BACKGROUND OF THE INVENTION

Asthma is a complex disease involving the concerted actions of multiple inflammatory and immune cells, spasmogens, inflammatory mediators, inflammatory cytokines and growth factors. In recent practice there have been four major classes of compounds used in the treatment of asthma, namely bronchodilators (e.g., β-adrenoceptor agonists), anti-inflammatory agents (e.g., corticosteroids), prophylactic anti-allergic agents (e.g., cromolyn sodium) and xanthines (e.g., theophylline) which appear to possess both bronchodilating and anti-inflammatory activity.

Theophylline has been a preferred drug of first choice in the treatment of asthma. Although it has been touted for its direct bronchodilatory action, theophylline's therapeutic value is now believed to also stem from anti-inflammatory activity. Its mechanism of action remains unclear. However, it is believed that several of its cellular activities are important in its activity as an anti-asthmatic, including cyclic nucleotide phosphodiesterase inhibition, adenosine receptor antagonism, stimulation of catecholamine release, and its ability to increase the number and activity of suppressor T-lymphocytes. While all of these may actually contribute to its activity, only PDE inhibition may account for both the anti-inflammatory and bronchodilatory components. However, theophylline is known to have a narrow therapeutic index and a wide range of untoward side effects which are considered problematic.

Of the activities mentioned above, theophylline's activity in inhibiting cyclic nucleotide phosphodiesterase has received considerable attention recently. Cyclic nucleotide phosphodiesterases (PDEs) have received considerable attention as molecular targets for anti-asthmatic agents. Cyclic 3',5'-adenosine monophosphate (cAMP) and cyclic 3',5'-guanosine monophosphate (cGMP) are known second messengers that mediate the functional responses of cells to a multitude of hormones, neurotransmitters and autocoids. At least two therapeutically important effects could result from phosphodiesterase inhibition, and the consequent rise in intracellular adenosine 3',5'-monophosphate (cAMP) or guanosine 3',5'-monophosphate (cGMP) in key cells in the pathophysiology of asthma. These are smooth muscle relaxation (resulting in bronchodilation) and anti-inflammatory activity.

It has become known that there are multiple, distinct PDE isoenzymes which differ in their cellular distribution. A variety of inhibitors possessing a marked degree of selectivity for one isoenzyme or the other have been synthesized.

The structure-activity relationships (SAR) of isozyme-selective inhibitors has been discussed in detail, e.g., in the article of Theodore J. Torphy, et al., "Novel Phosphodiesterases Inhibitors For The Therapy Of Asthma", Drug News & Prospectives, 6(4) May 1993, pages 203–214. The PDE enzymes can be grouped into five families according to their specificity toward hydrolysis of cAMP or cGMP, their sensitivity to regulation by calcium, calmodulin or cGMP, and their selective inhibition by various compounds. PDE I is stimulated by $Ca^{2+}$/calmodulin. PDE II is cGMP-stimulated, and is found in the heart and adrenals. PDE III is cGMP-inhibited, and inhibition of this enzyme creates positive inotropic activity. PDE IV is cAMP specific, and its inhibition causes airway relaxation, antiinflammatory and antidepressant activity. PDE V appears to be important in regulating cGMP content in vascular smooth muscle, and therefore PDE V inhibitors may have cardiovascular activity.

While there are compounds derived from numerous structure activity relationship studies which provide PDE III inhibition, the number of structural classes of PDE IV inhibitors is relatively limited. Analogues of rolipram, which has the following structural formula:

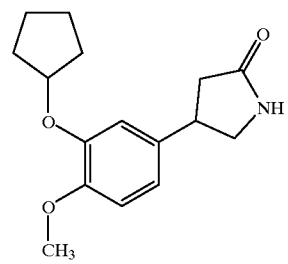

and of RO-20-1724, which has the following structural formula:

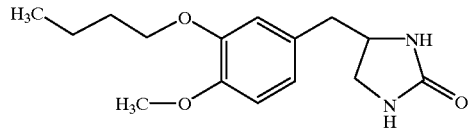

have been studied.

U.S. Pat. No. 4,308,278 discloses compounds of the formula (C)

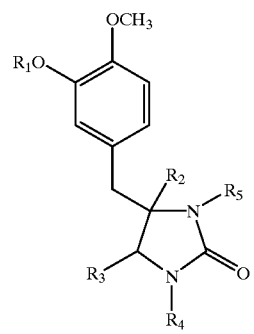

Wherein $R_1$ is ($C_3$–$C_6$) cycloalkyl or benzyl; each of $R_2$ and $R_3$ is hydrogen or ($C_1$–$C_4$) alkyl; $R_4$ is $R_2$ or alkoxycarbonyl; and $R_5$ is hydrogen or alkoxycarbonyl.

Compounds of Formula (D) are disclosed in U.S. Pat. No. 3,636,039. These compounds are benzylimidazolidinones which act as hypertensive agents.

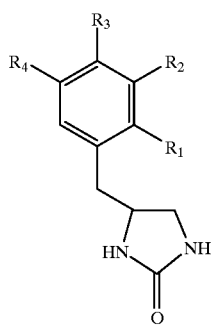

Formula D

Substituents $R_1$–$R_4$ in Formula D represent a variety of groups, including hydrogen and lower alkyl.

PCT publication WO 87/06576 discloses antidepressants of Formula E:

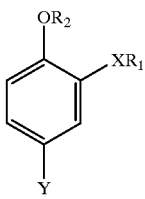

wherein $R_1$ is a polycycloalkyl group having from 7 to 11 carbon atoms; $R_2$ is methyl or ethyl; X is O or NH; and Y comprises of a mono-or bycyclic heterocyclic group with optional substituents.

Rolipram, which was initially studied because of its activity as an anti-depressant, has been shown to selectively inhibit the PDE IV enzyme and this compound has since become a standard agent in the classification of PDE enzyme subtypes. There appears to be considerable therapeutic potential for PDE IV inhibitors. Early work focused on depression as a CNS therapeutic endpoint and on inflammation, and has subsequently been extended to include related diseases such as dementia and asthma. In-vitro, rolipram, RO20-1724 and other PDE IV inhibitors have been shown to inhibit (1) mediator synthesis/release in mast cells, basophils, monocytes and eosinophils; (2) respiratory burst, chemotaxis and degranulation in neutrophils and eosinophils; and (3) mitogen-dependent growth and differentiation in lymphocytes (The PDE IV Family Of Calcium-Phosphodiesterases Enzymes, John A. Lowe, III, et al., Drugs of the Future 1992, 17(9):799–807).

PDE IV is present in all the major inflammatory cells in asthma including eosinophils, neutrophils, T-lymphocytes, macrophages and endothelial cells. Its inhibition causes down regulation of inflammatory cell activation and relaxes smooth muscle cells in the trachea and bronchus. On the other hand, inhibition of PDE III, which is present in myocardium, causes an increase in both the force and rate of cardiac contractility. These are undesirable side effects for an anti-inflammatory agent. Theophylline, a non-selective PDE inhibitor, inhibits both PDE III and PDE IV, resulting in both desirable anti-asthmatic effects and undesirable cardiovascular stimulation. With this well-known distinction between PDE isozymes, the opportunity for concomitant anti-inflammation and bronchodilation without many of the side effects associated with theophylline therapy is apparent. The increased incidence of morbidity and mortality due to asthma in many Western countries over the last decade has focused the clinical emphasis on the inflammatory nature of this disease and the benefit of inhaled steroids. Development of an agent that possesses both bronchodilatory and antiinflammatory properties would be most advantageous.

It appears that selective PDE IV inhibitors should be more effective with fewer side effects than theophylline. Clinical support has been shown for this hypothesis. Furthermore, it would be desirable to provide PDE IV inhibitors which are more potent and selective than theophylline and therefore have a lower $IC_{50}$ so as to reduce the amount of the agent required to effect PDE IV inhibition.

In recent years, several different compounds have been suggested as possible therapeutic compositions which achieve the desired PDE IV inhibition without the side effects alluded to above. However, these efforts have been chiefly directed to developing non-specific derivatives of particular classes of compounds, i.e. rolipram analogs, benzoxazoles, adenines, thioxanthines, etc. These efforts, however, have resulted in a myriad of compounds having a wide range of PDE IV $IC_{50}$'s. Often, the general formulas disclosed yield several compounds which have poor levels of PDE IV inhibition and/or lack sufficient specificity. Consequently, these efforts often provide no assurance that any particular derivative within the formula will have the desired combination of high PDE IV inhibition and selectivity.

OBJECTS AND SUMMARY OF THE INVENTION

It is accordingly a primary object of the present invention to provide new compounds which have a superior PDE IV inhibitory effect as compared to theophylline or other known compounds.

It is another object of the present invention to provide new compounds which act as effective PDE IV inhibitors with lower PDE III inhibition.

It is a further object of the present invention to provide new compounds which exhibit surprisingly greater selectivity with regard to their PDE IV inhibitory effects.

It is another object of the present invention to provide a method of treating a patient requiring PDE IV inhibition.

It is another object of the present invention to provide new compounds for treating disease states associated with abnormally high physiological levels of inflammatory cytokines, including tumor necrosis factor.

It is another object of the present invention to provide a method of synthesizing the new compounds of this invention.

With the above and other objects in view, one aspect of the invention includes PDE IV inhibitor compounds containing a fused 6,5-membered ring system with a substitution pattern that yields compounds having a high degree of selective PDE IV inhibition and an $IC_{50}$ below that of theophylline. The present invention includes compounds of Formula I:

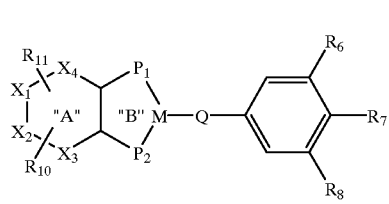

Formula I wherein:
rings "A" and "B" can be unsaturated or partially unsaturated;

$X_1$ is selected from CH, C—Cl, or N;

$X_2$ is selected from $CR_{12}$ or N;

$X_3$ is selected from CH or N;

$X_4$ is selected from CH or N; wherein at least one of $X_1$ to $X_4$ is N;

$P_1$, $P_2$ are independently selected from CH, O, N, or NH, provided that at least one of $P_1$ and $P_2$ is not CH;

M is selected from CH, C, or N;

Q is $C_1$–$C_3$-alkylene or —CH=CH—;

$R_6$ is selected from —$C(R_9)_3$, —$CH(R_9)_2$, or —$C_3$–$C_8$-cycloalkyl;

$R_7$ is selected from —SH, OH or $OCOR_9$, wherein $R_9$ is defined below;

$R_8$ is selected from —$C(R_9)_3$, —$CH(R_9)_2$, —$C_3$–$C_8$-cycloalkyl, or —$CH_2$—$C_4$–$C_6$-cycloalkyl;

$R_{10}$ is selected from —$C_1$–$C_3$-pyridyl, —$C_3H_6OH$, —C≡CH, Br, —C=C—$CH_2OH$, isopropyl, hydrogen,

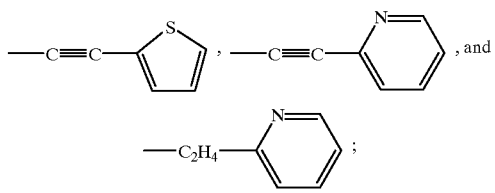

$R_{11}$ is selected from H, —OH, —O—$C_3$–$C_8$-cycloalkyl, —$C_3$-alkyl, —Z-pyridyl, —Z-thienyl, and —Z—$CH_2OH$;

$R_{12}$ is selected from —SH, H, halogen or lower alkyl;

$R_9$ is lower alkyl; and

Z is selected from ethylene, and —C=C—.

Other aspects of the invention include methods of synthesizing the compounds described above as well as pharmaceutical compositions containing the same. Still further aspects of the invention include methods of treating PDE IV-susceptible conditions in mammals by administering an effective amount of the compositions described herein.

DETAILED DESCRIPTION

The compounds of the present invention are effective in the selective mediation or inhibition of PDE IV in mammals. These compounds possess both bronchodilatory and antiinflammatory properties which are substantially without the undesirable cardiovascular stimulation which is caused by PDE III inhibition. The compounds of the present invention have a PDE IV inhibitory effect which is greater than rolipram or theophylline.

The PDE IV inhibitor compounds of the present invention are based on a fused 6,5-membered ring system compounds having a high degree of selective PDE IV inhibition and an $IC_{50}$ below that of theophylline. This selective blocking has been unexpectedly achieved by compounds of Formula I:

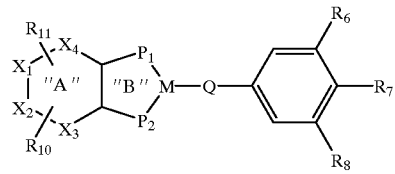

Formula I wherein:

rings "A" and "B" can be unsaturated or partially unsaturated;

$X_1$ is selected from CH, C—Cl, or N;

$X_2$ is selected from $CR_{12}$ or N;

$X_3$ is selected from CH or N;

$X_4$ is selected from CH or N; wherein at least one of $X_1$ to $X_4$ is N;

$P_1$, $P_2$ are independently selected from CH, O, N or NH, provided that at least one of $P_1$ and $P_2$ is not CH;

M is selected from CH, C, or N;

Q is $C_1$–$C_3$ alkylene or —CH=CH—;

$R_6$ is selected from —$C(R_9)_3$, —$CH(R_9)_2$, or —$C_3$—$C_8$-cycloalkyl;

$R_7$ is selected from —SH, or $OCOR_9$, wherein $R_9$ is defined below;

$R_8$ is selected from —$C(R_9)_3$, —$CH(R_9)_2$, —$C_3$–$C_8$-cycloalkyl, or —$CH_2$—$C_4$–$C_6$-cycloalkyl;

$R_{10}$ is selected from $C_1$–$C_3$-pyridyl, $C_3H_6OH$, —C≡CH, Br, —C=C—$CH_2OH$, isopropyl, hydrogen,

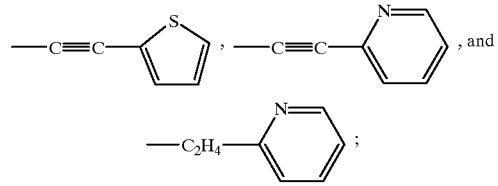

$R_{11}$ is selected from H, —OH, —O—$C_3$–$C_8$-cycloalkyl, —SH, —Z-pyridyl, —Z-thienyl, and —Z—$CH_2OH$;

$R_{12}$ is selected from —SH, H, halogen or lower alkyl;

$R_9$ is lower alkyl; and

Z is selected from ethylene, and —C=C—.

Preferred compounds have a structure of Formula II,

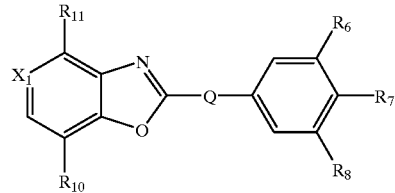

Formula II wherein $R_6$ is selected from —$C(R_9)_3$, —$CH(R_9)_2$, and $C_3$–$C_8$-cycloalkyl;

$R_7$ is selected from —OH, —SH, —O—CO—$CH_3$, and —CHO;

$R_8$ is selected from —$C(R_9)_3$, —$CH(R_9)_2$, and —$CH_2$—$C_4$–$C_6$-cycloalkyl;

Q is selected from —$C_1$-$C_2$-alkylene and —CH=CH—;
$R_{10}$ is selected from $C_1$-$C_3$-pyridyl, $C_3H_6OH$, —C≡CH, Br, —C≡C—$CH_2$OH—, isopropyl, hydrogen,

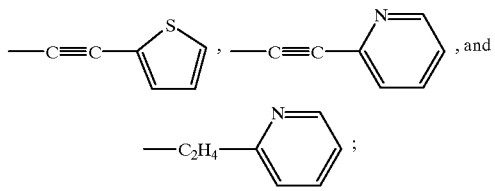

$R_{11}$ is selected from H, —OH, —O—$C_3$-$C_8$-cycloalkyl, —SH, —Z-pyridyl, —Z-thienyl, and —Z—$CH_2$OH;
$X_1$ is selected from CH and C—Cl;
$R_9$ is lower alkyl; and
Z is selected from ethylene and —C≡C—.
Further preferred are compounds of Formula II wherein
$R_6$ is selected from —$C(CH_3)_3$, and —$CH(CH_3)_2$;
$R_7$ is selected from —OH and —O—CO—$CH_3$;
$R_8$ is selected from —$C(CH_3)_3$, and —$CH(CH_3)_2$;
Q is selected from —$C_1$-$C_2$-alkylene and —CH=CH—;
$R_{10}$ is selected from $C_1$-$C_3$-pyridyl, $C_3H_6OH$, —C≡CH, Br, —C≡C—$CH_2$OH, isopropyl, hydrogen,

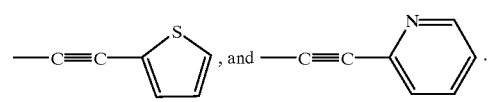

Particularly preferred compounds of the present invention include:
1. 5-chloro-2-(3,5-di-t-butyl-4-hydroxy-benzyl)-7-(2-(2-pyridyl)-ethynyl)-benzoxazole;
2. 2-(3,5-di-t-butyl-4-hydroxy benzyl)-7-(2-(2-pyridyl)-ethynyl)-benzoxazole;
3. 5-chloro-2-(3,5-di-t-butyl-4-hydroxy-benzyl)-7-(2-(2-thiazolyl)-ethynyl)-benzoxazole; and
4. 3-[5-chloro-2-(3,5-di-t-butyl-4-hydroxy-benzyl)-benzoxazol-7-yl]-propynol.

The present invention includes pharmaceutical compositions of compounds of Formula I and Formula II; methods of effecting selective PDE IV inhibition in mammals requiring the same, which comprises administering an effective amount of a compound of Formula I and Formula II; methods of treating a mammal suffering from a disease state selected from a group consisting of asthma, allergies, inflammation, dementia, atopic diseases, rhinitis, and disease states associated with abnormally high physiological levels of inflammatory cytokine, comprising administering an effective amount of a compound of Formula I and Formula II.

The present invention also includes pharmaceutically acceptable salts and prodrugs of all the compounds of the present invention. Pharmaceutically acceptable salts include those in which the main compound functions as a base, e.g., hydrochloride, as well as those for which the main compound functions as an acid, e.g., choline salts.

METHODS OF SYNTHESIS

The compositions of the present invention can be prepared using standard organic methods. See, for example, commonly assigned PCT/GB94/01334 having PCT International Publication No. WO 95/00516, the contents of which are hereby incorporated by reference. Details concerning preparing some of the preferred compounds are provided in the Examples section below.

METHODS OF TREATMENT

In view of the high degree of selective PDE IV inhibition, the compounds of the present invention can be administered to anyone requiring PDE IV inhibition. Administration may be accomplished orally, topically, by suppository, inhalation or insufflation, or parenterally.

The present invention also encompasses all pharmaceutically acceptable salts of the foregoing compounds. One skilled in the art will recognize that acid addition salts of the claimed compounds may be prepared by reaction of the compounds with the appropriate acid via a variety of known methods. Alternatively, alkali and alkaline earth metal salts are prepared by reaction of the compounds of the invention with the appropriate base via a variety of known methods. For example, the sodium salt of the compounds of the invention can be prepared via reacting the compound with sodium hydride.

Various oral dosage forms can be used, including such solid forms as tablets, gelcaps, capsules, caplets, granules, lozenges and bulk powders and liquid forms such as emulsions, solution and suspensions. The compounds of the present invention can be administered alone or can be combined with various pharmaceutically acceptable carriers and excipients known to those skilled in the art, including but not limited to diluents, suspending agents, solubilizers, binders, disintegrants, preservatives, coloring agents, lubricants and the like.

When the compounds of the present invention are incorporated into oral tablets, such tablets can be compressed, tablet triturates, enteric-coated, sugar-coated, film-coated, multiply compressed or multiply layered. Liquid oral dosage forms include aqueous and nonaqueous solutions, emulsions, suspensions, and solutions and/or suspensions reconstituted from non-effervescent granules, containing suitable solvents, preservatives, emulsifying agents, suspending agents, diluents, sweeteners, coloring agents, and flavorings agents. When the compounds of the present invention are to be injected parenterally, they may be, e.g., in the form of an isotonic sterile solution. Alternatively, when the compounds of the present invention are to be inhaled, they may be formulated into a dry aerosol or may be formulated into an aqueous or partially aqueous solution.

In addition, when the compounds of the present invention are incorporated into oral dosage forms, it is contemplated that such dosage forms may provide an immediate release of the compound in the gastrointestinal tract, or alternatively may provide a controlled and/or sustained release through the gastrointestinal tract. A wide variety of controlled and/or sustained release formulations are well known to those skilled in the art, and are contemplated for use in connection with the formulations of the present invention. The controlled and/or sustained release may be provided by, e.g., a coating on the oral dosage form or by incorporating the compound(s) of the invention into a controlled and/or sustained release matrix.

Specific examples of pharmaceutically acceptable carriers and excipients that may be used for formulate oral dosage forms, are described in the *Handbook of Pharmaceutical Excipients,* American Pharmaceutical Association (1986), incorporated by reference herein. Techniques and compositions for making solid oral dosage forms are described in Pharmaceutical Dosage Forms: Tablets (Lieberman, Lachman and Schwartz, editors) 2nd edition, published by Marcel Dekker, Inc., incorporated by reference herein. Techniques and compositions for making tablets (compressed and molded), capsules (hard and soft gelatin) and pills are also described in Remington's Pharmaceutical Sciences (Arthur Osol, editor), 1553–1593 (1980), incorporated herein by reference. Techniques and composition for making liquid oral dosage forms are described in Pharmaceutical Dosage Forms: Disperse Systems, (Lieberman, Rieger and Banker, editors) published by Marcel Dekker, Inc., incorporated herein by reference.

When the compounds of the present invention are incorporated for parenteral administration by injection (e.g., continuous infusion or bolus injection), the formulation for parenteral administration may be in the form of suspensions, solutions, emulsions in oily or aqueous vehicles, and such formulations may further comprise pharmaceutically necessary additives such as stabilizing agents, suspending agents, dispersing agents, and the like. The compounds of the invention may also be in the form of a powder for reconstitution as an injectable formulation.

The dose of the compounds of the present invention is dependent upon the affliction to be treated, the severity of the symptoms, the route of administration, the frequency of the dosage interval, the presence of any deleterious side-effects, and the particular compound utilized, among other things.

The present invention is further related to a method for the treatment of allergic and inflammatory disease which comprises administering to a mammal in need thereof an effective amount of the compounds of the present invention.

The present invention is also related to a method for the mediation or inhibition of the enzymatic or catalytic activity of PDE IV activity in mammals, particularly humans, which comprises administering an effective amount of the above-described compounds of the invention to a mammal in need of PDE IV inhibition.

The compounds of the present invention may find use in the treatment of other disease states in humans and other mammals, such as in the treatment of disease states associated with a physiologically detrimental excess of tumor necrosis factor (TNF). TNF activates monocytes, macrophages and T-lymphocytes. This activation has been implicated in the progression of Human Immunodeficiency Virus (HIV) infection and other disease states related to the production of TNF and other inflammatory cytokines modulated by TNF.

DESCRIPTION OF THE PREFERRED EMBODIMENTS

The following examples illustrate various aspects of the present invention, and are not to be construed to limit the claims in any manner whatsoever.

EXAMPLE 1

5-chloro-2-(3,5-di-t-butyl-4-hydroxy-benzyl)-7-(2-(2-pyridyl)-ethynyl)-benzoxazole (a) 2-bromo-4-chloro-6-nitro-phenol A solution of 2-bromo-4-chloro-phenol (99.24 g, 480 mmol) in acetic acid (110 ml) and acetic anhydride (125 ml) was cooled to −10 EC. Within 1 hour a solution containing 100% nitric acid (33 ml) and acetic acid (40 ml) was added between −10 E and −5 EC, with stirring. The mixture was stirred for an additional 1.5 hours at 0–5 EC, then the suspension poured onto 300 g of ice in 700 ml of water and stirred for a further 0.5 hour. The solid was collected, washed, and dried to give 97.12 g (80.1%) of the title compound (mp 121–2 EC).

(b) 6-amino-2-bromo-4-chloro-phenol

A solution of 2-bromo-4-chloro-6-nitro-phenol (16.27 g, 64.4 mmol) in ethyl acetate (160 ml) was hydrogenated, at room temperature, with Raney-nickel (6 g). After hydrogen uptake (approx. 4.8 l) was complete, the nickel was removed by filtration and the filtrate evaporated in-vacuo to give 14.19 g (99.0%) of the title compound which was suitable for the next step.

(c) N,O-di-(3,5-di-t-butyl-4-hydroxy-phenyl acetyl)-6-amino-2-bromo-4-chloro-phenol Water (173 ml) and sodium carbonate (33.24 g, 310 mmol) were added to a stirred ethereal solution (123 ml) of 6-amino-2-bromo-4-chloro-phenol (17.45 g, 78.4 mmol). After 15 minutes 3,5-di-t-butyl-4-hydroxy-phenyl acetyl chloride (47.60 g, 93.1%, 156.8 mmol) (prepared with thionyl chloride from the corresponding acid), was added at −5 E to 0 EC and stirring continued for a further 1.5 hours without cooling. The aqueous phase was adjusted to pH 8 and the layers separated. The organics were washed with 1 N HCl (100 ml) and saturated aqueous sodium bicarbonate solution (100 ml), dried ($Na_2SO_4$) and evaporated in—to give 58.1 g (103.6%) of the title compound which was suitable for the next step.

(d) 2-bromo-4-chloro-6-(3,5-di-t-butyl-4-hydroxy-phenyl acetyl-amino)-phenol

A solution of N,O-Di-(3,5-di-t-butyl-4-hydroxy-phenyl acetyl)-6-amino-2-bromo-4-chloro-phenol (58.1 g, 89.8 mmol) in methanol (400 ml) and potassium carbonate (24.78 g, 180 mmol) was stirred at room temperature for 10 minutes. The methanol was removed in-vacuo, the residue treated with 2 N HCl (180 ml, 360 mmol), and extracted with ethyl acetate (300 ml). The organics were dried ($Na_2SO_4$), evaporated in-vacuo, and the residue suspended in petroleum ether. The precipitate was collected to give 37.44 g (88.9%) of the title compound which was suitable for the next step.

(e) 7-bromo-5-chloro-2-(3,5-di-t-butyl-4-hydroxy-benzyl)-benzoxazole

A solution of 2-bromo-4-chloro-6-(3,5-di-t-butyl-4-hydroxy-phenyl acetyl-amino)-phenol (35.67 g, 76.1 mmol) and phosphorus oxychloride (41.8 ml, 457 mmol) in toluene was heated under reflux for 1 hour. Volatiles were removed in-vacuo and residual amounts of phosphorus oxychloride removed by azeotropic distillation with toluene (2×50 ml). The residue was taken up in acetone (50 ml) and ether (100 ml), and treated with water (100 ml) and saturated aqueous sodium bicarbonate solution (100 ml). The organic solvents were removed in-vacuo and the precipitate collected to give 33.36 g (93.6%) of crude benzoxazole. The crude benzoxazole was dissolved in dichloromethane (100 ml), filtered, and the filtrate diluted with methanol (100 ml). The dichloromethane was removed by distillation and the resulting crystals collected, washed, and dried in-vacuo to give 28.86 g (80.9%) of the title compound (mp 133–6 EC).

(f) 5-chloro-2-(3,5-di-t-butyl-4-hydroxy-benzyl)-7-ethynyl-benzoxazole

A suspension of 7-bromo-5-chloro-2-(3,5-di-t-butyl-4-hydroxy-benzyl)-benzoxazole (13.50 g, 30 mmol), trimethylsilylacetylene (4.41 g, 6.36 ml 45 mmol), bis(triphenylphosphine) palladium (II) dichloride (105 mg, 150 μmol) and copper (I) iodide (5.75 mg, 30 μmol) in triethylamine (60 ml) was heated at 90 EC, under argon, for 3 hours. The mixture was cooled to room temperature, diluted with water (375 ml) and the excess triethylamine removed in-vacuo. The solid was removed by filtration and the filtrate evaporated in-vacuo to give 14.00 g (100%) of crude trimethylsilylacetylene derivative. A suspension of the crude trimethylsilylacetylene derivative (14 g) in methanol (140 ml) and potassium carbonate (6.20 g, 45 mmol) was stirred at room temperature, under nitrogen, for 10 minutes; 2 N HCl (45 ml, 90 mmol) was added slowly and the formed suspension evaporated in-vacuo. The residue was taken up in dichloromethane (200 ml), the salt removed by filtration and the filtrate evaporated in-vacuo to give 12.21 g (102.8%) of crude 5-chloro-2-(3,5-di-t-butyl-4-hydroxy-benzyl)-7-ethynyl-benzoxazole. The crude ethynyl-benzoxazole was dissolved in dichloromethane (40 ml) and filtered through 60 g of silica gel. The product was recrystallized from methanol to give 8.10 g (68.2%) of the title compound (mp 152–5 EC). From the filtrate a second crop of 1.31 g (11.0%) was also obtained.

Elemental analysis for $C_{24}H_{26}ClNO_2$ Calc. C 72.81 H 6.62 N 3.54 O 8.10 Found C 72.26 H 6.60 N 3.72 O 8.07

(g) 5-chloro-2-(3,5-di-t-butyl-4-hydroxy-benzyl)-7-(2-(2-pyridyl)-ethynyl)-benzoxazole A suspension of 5-chloro-2-(3,5-di-t-butyl-4-hydroxy-benzyl)-7-ethynyl-benzoxazole (2.38 g, 6.0 mmol), 2-bromo-pyridine (0.66 ml, 98%, 6.6 mmol), bis(triphenylphosphine)palladium(II) dichloride (21.1 mg, 30 μmol) and copper (I) iodide (1.2 mg, 6 μmol) in triethylamine (12 ml) was heated at 90 EC, under argon, for 1.5 hours. The triethylamine was removed in-vacuo and the residue dissolved in ether (100 ml). The organics were washed with water (50 ml), 1 N HCl (100 ml) and saturated aqueous sodium hydrogen carbonate (100 ml), dried $(Na_2SO_4)$ and evaporated in-vacuo to give 2.96 g (104.2%) of crude pyridyl ethynyl benzoxazole. The crude benzoxazole was purified by column chromatography $(SiO_2;$ dichloromethane), and the product crystallized from methanol and suspended in hot water. The resulting crystals were collected, washed, and dried to give 1.49 g (52.5%) of the title compound (mp 138–9 EC).

Elemental analysis for $C_{29}H_{29}ClN_2O_2$ Calc. C 73.64 H 6.18 N 5.92 O 6.76 Found C 73.62 H 5.97 N 5.91 O 6.93

EXAMPLE 2

2-(3,5di-t-butyl-4-hydroxy benzyl)-7-(2-(2-pyridyl)-ethynyl)-benzoxazole (a) 2-Bromo-6(3,5-di-t-butyl-4-hydroxy phenyl)acetylamido-phenol (3,5-di-t-butyl-4-hydroxy phenyl)acetic acid (5.03 g, 0.019 mol) in dichloromethane (20 ml) was added drop wise over 0.25 h to a stirred solution of carbonyl diimidazole (4.68 g, 0.029 mol) in dichloromethane (60 ml). After 2 h this solution was added drop wise over 0.5 h to a solution of 6-amino-2-bromophenol (4.30 g of a mixture containing 6-amino-2-dibromophenol (3.60 g, 0.019 mmol), and 6-amino-2,6-dibromophenol (0.70 g, 0.003 mol)) in dichloromethane (30 ml). After 18 h the reaction mixture was diluted with ethyl acetate (200 ml) and washed with 2 M hydrochloric acid (100 ml), and water, dried over magnesium sulfate, evaporated in vacuo, and purified by flash chromatography $(SiO_2,$ dichloromethane) to furnish a 4:1 w/w (as judged by $^1$H-NMR) mixture of 2-bromo-6-(3,5-di-t-butyl-4-hydroxy phenyl)acetylamido-phenol and 2,4-dibromo-6-(3,5-di-t-butyl-4-hydroxy phenyl)acetylamido-phenol (6.90 g) as a pale pink solid.

$\delta_H$ (250 MHz; $d_6$ DMSO) 1.37 (18 H, s, 2 x (—$CH_3)_3$, 3.62 (2 H, s, Ar—$CH_2$—), 6.78 (1 H, dd, Ar—H), 6.88 (1 H, s, —OH) 7.09 (2 H, s, 2'-,6'-H), 7.33 (1 H, dd, Ar—H), 7.43 (1 H, dd, 6-H), 9.92 (1 H, bs, —NH—), 10.02 (1 H, s, —OH).

A signal at δ=7.51 ppm (d) is attributable to 2,4-dibromo-6-(3,5-di-t-butyl-4-hydroxy phenyl)-acetylamido-phenol.

(b) 7-Bromo-2-((3,5-di-t-butyl-4-hydroxy)benzyl)-benzoxazole

2-Bromo-6-(3,5-di-t-butyl-4-hydroxy phenyl) acetylamido-phenol (6.90 g, 80%, 0.013 mol) and pyridinium toluene sulfonate (1.37 g, 0.0055 mol) were suspended in xylene (165 ml) and heated to reflux. After 17 h the reaction mixture was allowed to cool, diluted with water (200 ml) and extracted with ethyl acetate (3× 100 ml). The organic extracts were combined, dried over magnesium sulfite, evaporated in vacuo and purified by flash chromatography $(SiO_2,$ dichloromethane/petrol 2:1 v/v) to afford the title compound (4.90 g, 0.0015 mol, 92%) as an off-white solid.

NMR: $\delta_H$ (250 MHz; $d_6$ DMSO) 1.35 (18 H, s, 2 x (—$CH_3)_3$), 4.24 (2 H, s, Ar—$CH_2$—), 6.95 (1 H, s, —OH) 7.14 (2 H, s, 2'-,6'-H), 7.28 (1 H, dd, 5-H), 7.57 (1 H, dd, 6-H), 7.69 (1 H, dd, Ar—H).

(c) 2-(3,5-di-t-butyl-4-hydroxy benzyl)-7-(2-(2-pyridyl)-ethynyl)-benzoxazole

Argon was bubbled through a mixture of 7-bromo-2-((3,5-di-t-butyl-4-hydroxy)benzyl)-benzoxazole, (1.002 g, 0.0024 mol), copper(I) iodide (2 mg), and 2-ethynylpyridine (0.320 ml, 0.326 g, 0.0032 mol) in triethylamine (6 ml). After 0.75 h bis(triphenylphosphine)palladium(II) dichloride (0.045 g, 0.00006 mol) was added and the reaction mixture was flushed with argon for a further 5 minutes then heated to 90 EC. After 1.5 h a new product was observed by TLC $(SiO_2,$ petrol/diethyl ether 1:1 v/v) together with both starting materials. Further portions of 2-ethynylpyridine were added after 2 h (0.100 ml, 0.102 g, 0.0099 mol) and 4.5 h (0.200 ml, 0.204 g, 0.0020 mol). No change was observed by TLC. An additional portion of bis(triphenylphosphine) palladium(II) dichloride (0.02 g, 0.00003 mol) was also added after 4.5 h and the mixture was stirred at 90 EC for a further 3 h and at ambient temperature for a further 16 h. No change was observed by TLC. The reaction mixture was evaporated in vacuo and purified by flash chromatography $(SiO_2,$ petrol/ether 1:1 v/v) to furnish the title compound (0.225 g, 0.00051 mol, 21%) as a dry khaki foam.

NMR: $\delta_H$ (250 MHz; $d_6$ DMSO) 1.35 (18 H, s, 2 x —C($CH_3)_3$), 4.27 (2 H, s, Ar—$CH_2$), 6.89 (1 H, bd, —OH), 7.17 (2 H, s, 2'-H and 6'-H), 7.41 (1 H, dd, 5-H), 7.47 (1 H, m, Py—H), 7.60 (1 H, d, Ar—H), 7.68. (1 H, d, Py—H), 7.76 (1 H, d, Ar—H), 7.89 (1 H, m, Py—H), 8.64 (1 H, m, Py—H).

ν(KBr Disc) 3633, 3450, 2956, 2927, 2912, 2871, 2221, 1604, 1582, 1564, 1488, 1462, 1424, 1400, 1390, 1361, 1315, 1279, 1259, 1236, 1212, 1189, 1148, 1136, 1121, 1095, 1048, 1036, 989, 822, 795, 776, 741 $cm^{-1}$.

EXAMPLE 3

5-chloro-2-(3,5di-t-butyl-4-hydroxy-benzyl)-7-(2-(2-thiazolyl)-ethynyl)-benzoxazole A suspension of 5-chloro-2-(3,5-di-t-butyl-4-hydroxy-benzyl)-7-ethynyl-benzoxazole (2.38 g, 6.0 mmol), 2-bromothiazole (1.13 ml, 95%, 12 mmol), bistriphenylphosphine)palladium(II) dichloride (21.1 mg, 30 μmol), and copper (I) iodide (1.2 mg, 6 μmol) in triethylamine (12 ml) was heated at 90 EC, under argon, for 3 hours. The triethylamine was removed in-vacuo and the residue dissolved in ether (70 ml) and water (30 ml). The organics were washed with 1 N HCl (30 ml) and saturated sodium hydrogen carbonate (30 ml), dried $(Na_2SO_4)$ and evaporated—to give 2.86 g (100%) of crude thiazolylethynylbenzoxazole, which was purified by flash chromatography ($SiO_2$; dichloromethane). The product was crystallized and recrystallized from methanol to give 1.43 g (50.4%) of the title compound (mp 137–41 EC).

Elemental analysis for $C_{27}H_{27}ClN_2O_2S$ Calc. C 67.70 H 5.68 N 5.85 O 6.68 Found C 67.62 H 5.40 N 5.65 O 6.76

EXAMPLE 4

3-[5-chloro-2-(3,5-di-t-butyl-4 hydroxy-benzyl) benzoxazol-7-yl]propynol

This compound can be synthesized by the methods outlined for examples 1–3.

Enzyme Isolation Protocol

Protocols for PDE III and PDE IV inhibition activity are set forth below:

Type III Phosphodiesterase

The Type III PDE is isolated from human platelets using a procedure similar to that previously described by Weishaar, R. E.; Burrows, S. D.; Kobylarg, D. C., Quade, N. M.; Evans, D. B., Biochem. Pharmacol., 35:787, 1986. Briefly, 1–2 units of platelets are suspended in an equal volume of buffer (20 mM Tris-HCl, pH 7.5, containing 2 mM magnesium acetate, 1 mM dithiothreitol, and 5 mM $Na_2$ EDTA). The protease inhibitor phenyl methyl-sulfonyl fluoride (PMSF) is also included in this buffer at a final concentration of 200 $\mu$M. The suspension is homogenized using a polytron and the homogenate centrifuged at 100,000×g for 60 minutes. This and all subsequent procedures are performed at 0–4 EC. The supernatant is then filtered through four layers of gauze and applied to a DEAE-Trisacryl M column, previously equilibrated with buffer B (20 mM Tris-HCl, pH 7.5, containing 1 mM magnesium acetate, 1 mM dithiothreitol and 200 $\mu$M PMSF). After application of the sample, the column is washed with several bed volumes of buffer B, after which the different forms of PDE are eluted from the column using two successive linear NaCl gradients (0.05–0.15 M, 300 ml total; 0.15–0.40 M, 200 ml total). Five milliliter fractions are collected and assayed for cyclic AMP and cyclic GMP PDE activity. Fractions containing PDE III activity are pooled and dialyzed overnight against 4 liters of buffer B. The dialyzed PDE III is then concentrated to 10% of the original volume, diluted to 50% with ethylene glycol monoethyl ether and stored at –20 EC. PDE III can typically be retained for up to four weeks with little or no loss of activity.

Measuring Type III PDE Activity

Enzyme activity is assessed by measuring the hydrolysis of [$^3$H]-cyclic AMP, as described by Thompson, W. J., Teraski, W. L., Epstein, P. N., Strada, S. J.: Adv. Cyclic Nucleotide Res. 10:69, 1979. The cyclic AMP concentration used in this assay is 0.2 $\mu$M, which approximates to the $K_m$ value. Protein concentration is adjusted to ensure that no more than 15% of the available substrate is hydrolyzed during the incubation period.

All test compounds are dissolved in dimethyl sulfoxide (final concentration of 2.5%). This concentration of dimethyl sulfoxide inhibits enzyme activity by approximately 10%.

Type IV Phosphodiesterase

Enzyme Isolation Protocol

The Type IV PDE is isolated from bovine tracheal smooth muscle using a procedure similar to that previously described by Silver, P. J., et al.: Eur. J. Pharmacol. 150:85, 1988.(1). Briefly, smooth muscle from bovine trachea is minced and homogenized using a polytron in 10 volumes of an extraction buffer containing 10 mM Tris-acetate (pH 7.5), 2 mM magnesium chloride, 1 mM dithiothreitol and 2,000 units/ml of aprotinin. This and all subsequent procedures are performed at 0–4 EC. The homogenate is sonicated and then centrifuged at 48,000×g for 30 minutes. The resulting supernatant is applied to a DEAE Trisacryl M column previously equilibrated with sodium acetate and dithiothreitol. After applications of the sample, the column is washed with sodium acetate/dithiothreitol, after which the different forms of PDE are eluted from the column using a linear Tris-HCl/NaCl gradient. Fractions containing Type IV PDE are collected, dialyzed and concentrated to 14% of the original volume. The concentrated fractions are diluted to 50% with ethylene glycol and stored at –20 EC.

Measuring Type IV PDE Activity

Enzyme activity is assessed by measuring the hydrolysis of [$^3$H]-cyclic AMP, as described by Thompson, W. J., et al.: Adv. Cyclic Nucleotide Res. 10:69, 1979. The cyclic AMP concentration used in this assay is 0.2 $\mu$M, which approximates to the $K_m$ value. Protein concentration is adjusted to ensure that no more than 15% of the available substrate is hydrolyzed during the incubation period.

All test compounds are dissolved in dimethyl sulfoxide (final concentration of 2.5%). This concentration of dimethyl sulfoxide inhibits enzyme activity by approximately 10%.

Measuring Type V PDE Activity

Enzyme Isolation Protocol

The Type V PDE is isolated using a procedure similar to that previously described by Weishaar et al., Hypertension 15:528, (1990). Briefly, 1–2 units of platelets are suspended in an equal volume of buffer A (20 mM Tris-HCl, pH 7.5, containing 2 mM magnesium acetate, 1 mM dithiothreitol, and 5 mM $Na_2$EDTA) using a polytron. The proteinase inhibitor phenylmethylsulfonyl fluoride (PMSF) are also included in this buffer at a final concentration of 200 uM. This and all subsequent procedures are performed at 0–4 EC. The homogenate is then centrifuged at 100,000 rpm for 60 minutes. The supernatant is then removed and filtered through four layers of gauze and applied to a DEAE-Trisacryl M column. The column is washed with several bed volumes of buffer B (20 mM Tris-HCl, pH 7.5, containing 2 mM magnesium acetate, 1 mM diothiothreitol, and 200 mM PMSF) and eluted by two successive linear NaCl gradients (0.05–0.15 M, 300 ml total; 0.15–0.40 M, 200 ml total). Five ml fractions are collected and assayed for cyclic AMP and cyclic GMP PDE activity. Fractions that contain PDE V are pooled and dialyzed overnight against 4 L of buffer C (20 mM Tris-HCl, pH 7.5, containing 2 mM magnesium acetate and proteinase inhibitors). The dialyzed PDE V is then concentrated to 10% of the original volume, diluted to 50% with ethylene glycol monoethyl ether and stored at –20 EC. PDE V can typically be retained for up to four weeks with little or no loss of activity.

Measuring Type V PDE Activity

Enzyme activity is assessed by measuring the hydrolysis of [$^3$H]-cyclic GMP, as described by Thompson et al. (Thompson, W. J., Teraski, W. L., Epstein, P. N., Strada, S. J.: Adv. Cyclic Nucleotide Res. 10:69, 1979). The cyclic GMP concentration used in this assay is 0.2 $\mu$M, which approximates to the $K_m$ value. Protein concentration is adjusted to ensure that no more than 15% of the available substrate is hydrolyzed during the incubation period.

All test compounds are dissolved in dimethyl sulfoxide (final concentration of 2.5%). This concentration of dimethyl sulfoxide inhibits enzyme activity by approximately 10%. The reference Type V PDE inhibitor zaprinast is evaluated with each assay.

The compounds are tested over concentration range: 0.1, 1, 10, 100 uM (n=1), and $IC_{50}$ determinations are made using 5 appropriate concentrations (n=2).

As can be seen from the foregoing, the compositions of the present invention are also potent inhibitors of PDE V in mammals. Such activity is useful in the medical arts to reduce smooth muscle cell proliferation and increase pulmonary vasodilation. In certain aspects of the invention, the compounds demonstrate a combination of selective PDE IV and PDE V inhibition and can be used in diseases such as restenosis and related diseases. Such aspects, of course, include administering an effective amount of a compound of the present invention possessing said combination of PDE IV and V inhibitory activities to a mammal in need of such therapy.

Following the above procedures, the PDE III, PDE IV and PDE V inhibition for the compounds of Examples 1–4 Theophylline and Rolipram were tested and compared. The results are shown the Table I below:

Following the above procedures, the PDE III, PDE IV and PDE V] inhibition for the compounds of Examples 1–4 and rolipram were tested and compared. The results are shown the Table below:

TABLE

| EXAMPLE | PDE IV $IC_{50}$ (μm) | PDE III $IC_{50}$ (μm) | PDE V $IC_{50}$ (μm) |
|---|---|---|---|
| 1 | 0.013 | >300 | >300 |
| 2 | 0.70 | >300 | 35.1 |
| 3 | 0.014 | >300 | >300 |
| 4 | 0.42 | >300 | 19.5 |
| Rolipram | 3.7 | 620 | 500 |
| Theophylline | 321 | 380 | 750 |

As can be seen from the foregoing, the inventive compounds provide high levels of PDE-IV inhibition and low levels of PDE-III inhibition. In all cases, the PDE-IV $IC_{50}$ values were below that of rolipram and the PDE-III and PDE V values were all at levels which are associated with low levels of inhibition.

While the invention has been illustrated with respect to the production and of particular compounds, it is apparent that variations and modifications of the invention can be made without departing from the spirit or scope of the invention.

We claim:

1. A compound of Formula I:

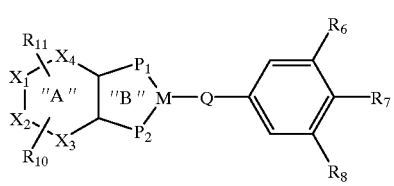

Formula I wherein:
rings "A" and "B" are unsaturated or partially unsaturated;
$X_1$ is selected from CH, C—Cl, or N;
$X_2$ is selected from $CR_{12}$ or N;
$X_3$ is selected from CH or N;
$X_4$ is selected from CH or N, wherein at least one of $X_1$ to $X_4$ is N;
$P_1$, $P_2$ are independently selected from CH, O, N or NH, provided that at least one of $P_1$ and $P_2$ is not CH;
M is selected from CH, C, or N;
Q is $C_1$-$C_3$ alkylene or —CH=CH—;
$R_6$ is selected from —C($R_9$)$_3$, —CH($R_9$)$_2$, or —$C_3$-$C_8$-cycloalkyl;
$R_7$ is selected from —SH, OH or $OCOR_9$, wherein $R_9$ is defined below;
$R_8$ is selected from —C($R_9$)$_3$, —CH($R_9$)$_2$, —$C_3$-$C_8$-cycloalkyl, or —CH$_2$—$C_4$-$C_6$-cycloalkyl;
$R_{10}$ is selected from $C_1$-$C_3$-pyridyl, $C_3H_6OH$, —C≡CH, Br, —C≡C—CH$_2$OH, isopropyl, hydrogen,

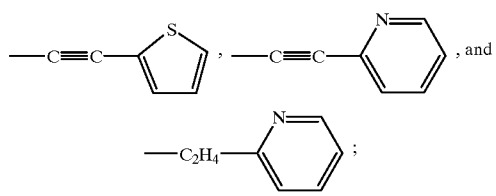

$R_{11}$ is selected from H, —OH, —O—$C_3$-$C_8$-cycloalkyl, —SH, —Z-pyridyl, —Z-thienyl, and —Z—CH$_2$OH;
$R_{12}$ is selected from —SH, H, halogen or lower alkyl;
$R_9$ is lower alkyl; and
Z is selected from ethylene, and —C≡C—, and pharmaceutically acceptable salts thereof.

2. A compound of claim 1, wherein
$R_6$ is selected from —C(CH$_3$)$_3$, and —CH(CH$_3$)$_2$;
$R_7$ is selected from —OH and —O—CO—CH$_3$;
$R_8$ is selected from —C(CH$_3$)$_3$, and —CH(CH$_3$)$_2$;
Q is selected from —$C_1$-$C_2$-alkyl and —CH=CH—;
$R_{10}$ is selected from —$C_1$-$C_3$-pyridyl, —$C_3H_6OH$,— C=CH, Br, —C≡C—CH$_2$OH, isopropyl, hydrogen,

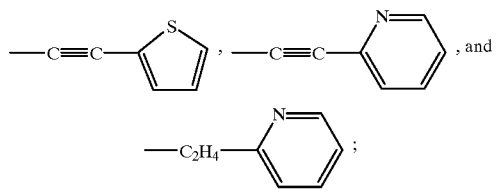

$R_{11}$ is selected from H and NH$_2$; and
$X_1$ is selected from CH or C—Cl.

3. A compound of claim 2, wherein $R_{11}$ is H.

4. A compound of claim 3, wherein $R_{10}$ is selected from isopropyl, propanol, —C=CH, —C=C—CH$_2$OH, $C_2$—H$_4$-pyridyl, Br,

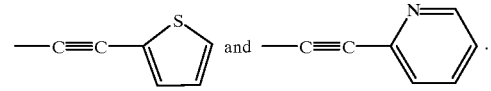

5. A pharmaceutical composition of a compound of claim 1 and a pharmaceutically acceptable carrier.

6. A method of effecting selective PDE IV inhibition in mammals requiring the same, which comprises administering an effective amount of a compound of Formula I of claim 1.

7. A method of treating a mammal suffering from a disease state selected from a group consisting of asthma, allergies, inflammation, dementia, atopic diseases, rhinitis, and disease states associated with abnormally high physiological levels of inflammatory cytokine, comprising administering an effective amount of a compound of claim 1.

8. The compound of claim 1, wherein at least one of $X_1$ to $X_4$ is not N.

* * * * *